United States Patent [19]
Bär et al.

[11] Patent Number: 6,011,037
[45] Date of Patent: Jan. 4, 2000

[54] THIAZOLE DERIVATIVES WITH PHOSPHODIESTERASE-INHIBITING ACTION

[75] Inventors: Thomas Bär; Wolf-Rüdiger Ulrich, both of Konstanz, Germany

[73] Assignee: Byk Gulden Lomberg Chemische Fabrik GmbH, Konstanz, Germany

[21] Appl. No.: 09/147,740

[22] PCT Filed: Aug. 13, 1997

[86] PCT No.: PCT/EP97/04435

§ 371 Date: Feb. 26, 1999

§ 102(e) Date: Feb. 26, 1999

[87] PCT Pub. No.: WO98/08841

PCT Pub. Date: Mar. 5, 1998

[30] Foreign Application Priority Data

Aug. 26, 1996 [DE] Germany ............... 196 34 411
Aug. 28, 1996 [EP] European Pat. Off. ............ 96113737

[51] Int. Cl.[7] .................... C07D 401/14; C07D 307/86; C07D 417/04; A61K 31/425
[52] U.S. Cl. .................... 514/248; 514/249; 514/252; 514/253; 514/256; 514/259; 514/307; 514/314; 514/342; 514/365; 544/235; 544/238; 544/284; 544/333; 544/353; 544/405; 546/144; 546/148; 546/167; 546/152; 546/269.7; 546/270.4; 548/202; 548/203
[58] Field of Search .................... 514/248, 249, 514/252, 253, 256, 259, 307, 314, 342, 365; 546/144, 148, 167, 152, 269.7, 270.4; 544/235, 238, 284, 333, 353, 405; 548/202, 203

[56] References Cited

FOREIGN PATENT DOCUMENTS

| 513387 | 11/1992 | European Pat. Off. . |
| 600092 | 6/1994 | European Pat. Off. . |
| 636626 | 2/1995 | European Pat. Off. . |
| WO 96/03392 | 2/1996 | WIPO . |

OTHER PUBLICATIONS

Palfreyman et al., Phosphodiesterase Type IV Inhibitors, Progress in Medicinal Chemistry, vol. 33, pp. 1–52, 1996.

Dumaitre et al., Synthesis and Cyclic GMP Phosphodiesterase Inhibitory Activity of a series of 6–phenylpyrazolo [3,4–d]pyrimidones, J. Med. Chem. 1996, 39, pp. 1635–1644.

Chihiro et al., Novel thiazole derivatives aas inhibitors of Superoxide production by human neurophils, J. Med. Chem., 38, pp. 353–358, 1995.

*Primary Examiner*—Mukund J. Shah
*Assistant Examiner*—Deepak R. Rao
*Attorney, Agent, or Firm*—Jacobson, Price, Holman & Stern, PLLC

[57] ABSTRACT

Compounds having the formula (I):

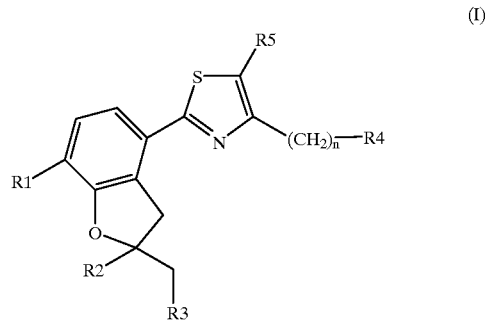

wherein R1, R2, R3, R4, R5 and n have the meanings given in the description. The compounds of formula (I) are selective inhibitors of phosphodiesterase IV.

11 Claims, No Drawings

THIAZOLE DERIVATIVES WITH PHOSPHODIESTERASE-INHIBITING ACTION

This application is a 371 of PCT/EP97/04435, filed Aug. 13, 1997,

FIELD OF APPLICATION OF THE INVENTION

The invention relates to novel thiazole derivatives which are used in the pharmaceutical industry for the production of medicaments.

KNOWN TECHNICAL BACKGROUND

Japanese Patent Specification JP 46-15935 describes substituted 4-(carboxyphenyl)thiazoles and their use for the treatment of thrombosis, arteriosclerosis, gastric ulcers and hypersecretion. European Patent Applications EP 0 513 387 and EP 0 600 092 describe, inter alia, 2-(substituted phenyl) thiazole derivatives, 2-(substituted 2, 3-dihydrobenzofuran) thiazole derivatives and their use as inhibitors of oxygen free radical release by neutrophils. The compounds are therefore described as suitable for the treatment of acute inflammatory processes such as ischemias and reperfusion damage.

DESCRIPTION OF THE INVENTION

It has now surprisingly been found that the novel thiazole derivatives described in greater detail below, which differ from the previously published thiazoles, in particular by the subtituents on the 2-(2,3-dihydrobenzofuran) ring, are selective inhibitors of phosphodiesterase IV.

The invention thus relates to compounds of the formula I, in which

R1 is 1-4C-alkoxy, 3-7C-cycloalkoxy, 3-7C-cycloalkylmethoxy, benzyloxy or 1-4C-alkoxy which is completely or mainly substituted by fluorine, R2 is hydrogen or 1-4C-alkyl and R3 is hydrogen or 1-4C-alkyl, or R2 and R3, together and including the two carbon atoms to which they are bonded, are a 5-, 6- or 7-membered hydrocarbon ring, if desired interrupted by an oxygen atom, R4 is a phenyl ring substituted by R41, R42 and R43, a mono- or bicyclic heterocycle substituted by R44, R45 and R46, which is selected from the group consisting of pyridine, pyrrole, quinoline, isoquinoline, indole, isoindole, indolizine, pyrimidine, pyrazine, pyridazine, quinoxaline, quinazoline, cinnoline, benzimidazole, thiophene and furan or a heterocycle substituted by R44 and R45, which is selected from the group consisting of pyrazole, imidazole, oxazole, isoxazole, thiazole and isothiazole, where R41 is hydrogen, carboxyl, 1-4C-alkoxycarbonyl, carbamoyl, hydroxysulfonyl, sulfamoyl, mono- or di-1-4C-alkylaminocarbonyl, mono- or di-1-4C-alkylaminosulfonyl, amino, mono- or di-1-4C-alkylamino, 1-4C-alkylcarbonylamino, 1-4C-alkylsulfonyl, 1-4C-alkoxysulfonyl, hydroxy-1-4C-alkyl, hydroxyl, 1-4C-alkoxy, 1-4C-alkyl, 1-4C-alkylcarbonyl, 1-4C-alkylcarbonyloxy, halogen, cyano or nitro, R42 is hydrogen, hydroxyl, amino, mono- or di-1-4C-alkylamino, 1-4C-alkylcarbonylamino, nitro, halogen, 1-4C-alkoxycarbonyl, 1-4C-alkylcarbonyloxy, 1-4C-alkylcarbonyl, carboxyl, 1-4C-alkyl or 1-4C-alkoxy, R43 is hydrogen, 1-4C-alkoxy, halogen or hydroxyl, R44 is hydrogen, carboxyl, 1-4C-alkoxycarbonyl, carbamoyl, hydroxysulfonyl, sulfamoyl, mono- or di-1-4C-alkylaminocarbonyl, mono- or di-1-4C-alkylaminosulfonyl, amino, mono- or di-1-4C-alkylamino, 1-4C-alkylcarbonylamino, hydroxy-1-4C-alkyl, hydroxyl, 1-4C-alkoxy, 1-4C-alkyl, 1-4C-alkylcarbonyl, 1-4C-alkylcarbonyloxy, halogen, cyano or nitro, R45 is hydrogen, hydroxyl, halogen, carboxyl, amino, 1-4C-alkyl, 1-4C-alkylcarbonyl, 1-4C-alkoxycarbonyl or 1-4C-alkoxy and R46 is hydrogen, halogen, 1-4C-alkoxy or 1-4C-alkyl, R5 is hydrogen or halogen, n is 0, 1 or 2, the salts of these compounds and the N-oxides of the pyridines, quinolines, isoquinolines, pyrimidines, pyrazines, imidazoles, quinoxalines, quinazolines and benzimidazoles and their salts.

1-4C-alkoxy represents a radical which, in addition to the oxygen atom, contains a straight-chain or branched alkyl radical having 1 to 4 carbon atoms. Alkyl radicals having 1 to 4 carbon atoms which may be mentioned here are, for example, the butyl, isobutyl, sec-butyl, tert-butyl, propyl, isopropyl, ethyl and the methyl 2-radicals.

3-7C-cycloalkoxy represents the cyclopropyloxy, cyclobutyloxy, cyclopentyloxy, cyclohexyloxy or cycloheptyloxy radical. The 3-5C-cycloalkoxy radicals cyclopropyloxy, cyclobutyloxy and cyclopentyloxy may preferably be mentioned.

3-7C-cycloalkylmethoxy is, for example, cyclopropylmethoxy, cyclobutylmethoxy, cyclopentylmethoxy, cyclohexylmethoxy or cycloheptylmethoxy. The 3-5C-cycloalkylmethoxy radicals, cyclopropylmethoxy, cyclobutylmethoxy and cyclopentylmethoxy may preferably be mentioned.

1-4C-alkoxy completely or mainly substituted by fluorine which may be mentioned is, for example, the 1,2,2,-trifluoroethoxy, the 2,2,3,3,3-pentafluoro-ethoxy, the perfluoroethoxy and in particular the 1,1,2,2-tetrafluoroethoxy, the trifluoromethoxy, the 2,2,2-trifluoroethoxy and preferably the difluoro-methoxy radicals.

1-4C-alkyl represents straight-chain or branched alkyl radicals having 1 to 4 carbon atoms. The examples which may be mentioned are the butyl, the isobutyl, the sec-butyl, the tert-butyl, the propyl, the isopropyl, the ethyl and in particular the methyl radicals.

A 5-, 6- or 7-membered hydrocarbon ring, if desired interrupted by an oxygen atom, which may be mentioned is the cyclopentane, the cyclohexane, the cycloheptane, the tetrahydrofuran and the tetrahydropyran rings. If R2 and R3 together and including the two carbon atoms to which they are bonded form a 5-, 6- or 7-membered ring, a spiro compound is present.

Halogen within the meaning of the invention is fluorine, chlorine, bromine or iodine.

Mono- or di-1-4C-alkylamino radicals which may be mentioned, for example, are the methylamino, the dimethylamino, the ethylaminio, the diethylamino, the propylamino or the isopropylamino radical.

Mono- or di-1-4C-alkylaminocarbonyl represents a carbonyl group to which one of the abovementioned mono- or di-1-4C-alkylamino radicals is bonded. The methylaminocarbonyl, the dimethylaminocarbonyl and the ethylaminocarbonyl radicals may be mentioned by way of example.

Mono- or di-1-4C-alkylaminosulfonyl represents a sulfonyl group to which one of the abovementioned mono- or di-1-4C-alkylamino radicals is bonded. The methylaminosulfonyl, the dimethylsulfonyl and the ethylaminosulfonyl radicals may be mentioned by way of example.

A 1-4C-alkylcarbonylamino radical which may be mentioned is, for example, the acetylamino radical (—NH—CO—CH$_3$).

1-4C-alkoxycarbonyl represents a carbonyl group to which one of the abovementioned 1-4C-alkoxy radicals is bonded. Examples which may be mentioned are the methoxycarbonyl radical (CH$_3$O—CO—) and the ethoxycarbonyl radical (CH$_3$CH$_2$O—CO—).

1-4C-alkylcarbonyl represents a carbonyl group to which one of the abovementioned 1-4C-alkyl radicals is bonded. An example which may be mentioned is the acetyl radical (CH$_3$—CO—).

In addition to the oxygen atom, 1-4C-alkylcarbonyloxy radicals contain a 1-4C-alkylcarbonyl radical. An example which may be mentioned is the acetoxy radical (CH$_3$CO—O—).

Hydroxy-1-4C-alkyl represents the abovementioned 1-4C-alkyl radicals which are substituted by a hydroxyl group. Examples which may be mentioned are the hydroxyethyl and the hydroxymethyl radicals.

1-4C-alkylsulfonyl represents a sulfonyl group to which one of the abovementioned 1-4C-alkyl radicals is bonded. An example which may be mentioned is the methylsulfonyl radical (CH$_3$SO$_2$—).

1-4C-alkoxysulfonyl represents a sulfonyl group to which one of the abovementioned 1-4C-alkoxy radicals is bonded. Examples which may be mentioned are the methoxysulfonyl radical (CH$_3$O—SO$_2$—) and the ethoxysulfonyl radical (CH$_3$CH$_2$O—SO$_2$—).

The linkage of the substituent R4 to the radical of the compounds of the formula I can take place via any suitable ring position of the phenyl ring or of the heterocycle.

By way of example of R4, the radicals phenyl, 4-acetamido-2-hydroxyphenyl, 6-acetamido-3-nitrophenyl, 3-acetoxyphenyl, 5-acetyl-2,4-dihydroxyphenyl, 3-acetylphenyl, 3-amino-4-hydroxyphenyl, 3-aminophenyl, 4-aminophenyl, 3,5-diaminophenyl, 2-bromo-4-carboxy-5-hydroxyphenyl, 2-carboxy-5-chlorophenyl, 3-carboxy-4-hydroxyphenyl, 2-carboxyphenyl, 3-carboxyphenyl, 4-carboxyphenyl, 2-cyanophenyl, 3-cyanophenyl, 3,5-diacetoxyphenyl, 3,5-diacetylphenyl, 2,4-dihydroxy-3-methylphenyl, 2,4-dihydroxyphenyl, 3,5-dihydroxy-phenyl, 2,3-dimethoxyphenyl, 2,4-dimethoxyphenyl, 2,4-dimethoxy-3-carboxyphenyl, 4-dimethylaminophenyl, 2-hydroxy-5-cyanophenyl, 4-hydroxy-3-methoxyphenyl, 4-hydroxy-3-methylphenyl, 4-hydroxy-3-nitrophenyl, 2-hydroxyphenyl, 3-hydroxyphenyl, 4-hydroxyphenyl, 2-hydroxy-4-methoxyphenyl, 2-methoxyphenyl, 4-methylsulfonylphenyl, 2-nitrophenyl, 3-nitrophenyl, 4-nitrophenyl, 2-sulfophenyl, 3-sulfophenyl, 4-sulfophenyl, 2,3,4-trihydroxyphenyl, 2-ethoxycarbonylphenyl, 3-ethoxycarbonylphenyl, 4-ethoxycarbonylphenyl, 2-carbamoylphenyl, 3-carbamoylphenyl, 4-carbamoylphenyl, 2-sulfamoylphenyl, 3-sulfamoylphenyl, 4-sulfamoylphenyl, 3-acetamido-4-hydroxyphenyl, 3,5-dinitro-4-hydroxyphenyl, 3,5-dimethyl-4-hydroxyphenyl, 2,4-diacetoxyphenyl, 3,5-dichloro-4-aminophenyl, 3-nitro-4-chlorophenyl, 3-methoxycarbonyl-5-nitrophenyl, 2-methoxycarbonyl-3-nitrophenyl, 2-amino-3-bromo-5-methoxycarbonylphenyl, 3-methylcarbonyloxy-5-methoxycarbonylphenyl, 2-methylcarbonyloxy-5-methoxycarbonylphenyl, 2-hydroxy-5-methoxycarbonylphenyl, 2-hydroxy-3-nitro-5-methoxycarbonylphenyl, 3-methoxycarbonyl-4-hydroxyphenyl, 3-nitro-4-hydroxy-5-methoxycarbonylphenyl, 2-hydroxy-3-methoxycarbonylphenyl, 3-methoxy-4-methoxycarbonylphenyl, 3-methyl-4-hydroxy-5-methoxycarbonylphenyl, 3-methoxycarbonyl-4-acetamidophenyl, 3-ethyl-4-hydroxyphenyl, 3-chloro-4-hydroxy-5-methoxycarbonylphenyl, 3,4-dihydroxyphenyl, 2,5-dimethoxyphenyl, 3-carboxyl-4-acetoxyphenyl, 2-hydroxy-3-propyl-5-carboxyphenyl, 3-carboxyl-4-hydroxy-5-propylphenyl, 2-methyl-4-hydroxy-5-carboxyphenyl, 3-ethyl-4-hydroxy-5-carboxyphenyl, 3-hydroxymethyl-4-hydroxyphenyl, 3-bromo-4-hydroxy-5-carboxyphenyl, 3-cyano-4-hydroxy-5-carboxyphenyl, 3,4-dihydroxy-5-carboxyphenyl, 3-acetamido-4-hydroxy-5-carboxyphenyl, 3,5-dicarboxy-4-hydroxyphenyl, 3-hydroxymethyl-4-dimethylaminophenyl, 3-hydroxymethyl-4-hydroxy-5-methoxycarbonylphenyl, 3-methoxycarbonyl-4-methoxyphenyl, 3-carboxy-4-dimethylaminophenyl, 3-methoxycarbonyl-4-dimethylaminophenyl, 3-acetamido-4-hydroxy-5-methoxycarbonylphenyl, 3-ethylamino-4-hydroxy-5-methoxycarbonylphenyl, 2-methyl-4-hydroxy-5-methoxycarbonylphenyl, 2-hydroxy-3-methoxycarbonyl-6-methylphenyl, 3-bromo-4-hydroxy-5-methoxycarbonylphenyl, 3,4-dimethoxyphenyl, 2,5-dihydroxyphenyl, 2,6-dihydroxyphenyl, 3-nitro-4-acetamidophenyl, 3,4-diacetamidophenyl, 2,4-dichlorophenyl, 4-chlorophenyl, 3,5-diamino-4-hydroxyphenyl, 4-fluorophenyl, 2,4,6-trihydroxyphenyl, 3,5-dinitrophenyl, 3,5-diacetamidophenyl, 4-cyanophenyl, 3,5-dimethylaminophenyl, 4-methylphenyl, 3,4-diacetoxyphenyl, 3-amino-4-carboxyphenyl, 3-carbamoyl-4-hydroxyphenyl, 3-methoxy-5-methoxycarbonylphenyl, 3-carboxy-5-methoxyphenyl, 3-amino-5-methoxycarbonylphenyl, 3-nitro-5-carboxyphenyl, 3-carboxy-5-aminophenyl, 2-hydroxy-3-carboxyphenyl, 3-methyl-4-hydroxy-5-carboxyphenyl, 3-carboxy-4-methoxyphenyl, 3-amino-4-hydroxy-5-methoxycarbonylphenyl, 3-amino-4-hydroxy-5-carboxyphenyl, 3-chloro-4-hydroxy-5-carboxyphenyl, 2-hydroxy-5-carboxyphenyl, 3-carboxy-4-acetamidophenyl, 3-carboxy-4-hydroxy-5-(2-hydroxyethyl)phenyl, 3-carboxy-4-aminophenyl, 3-hydroxy-5-carboxyphenyl, 3,5-dihydroxy-4-carboxyphenyl, 2,4-dihydroxy-5-carboxyphenyl, 2-methoxy-5-carboxyphenyl, 2-hydroxy-3-nitro-5-carboxyphenyl, 3-methoxycarbonyl-4-hydroxy-5-(2-hydroxyethyl)phenyl, 3-ethoxycarbonyl-4-acetamidophenyl, 3-methoxycarbonyl-5-hydroxyphenyl, 2-hydroxy-4-acetamido-5-methoxycarbonylphenyl, 2-methoxy-5-methoxycarbonylphenyl, 3-sulfo-4-methoxyphenyl, 5-methoxycarbonylpyrrol-2-yl, 5-methoxycarbonylfuran-2-yl, 2-ethoxycarbonyl-4-methylpyridin-6-yl, 5-ethoxycarbonylthiophen-2-yl, 3-methoxycarbonylpyridin-5-yl, 4-cyanopyridin-2-yl, 2-methyl-3-carbamoylpyridin-5-yl, 2-methoxycarbonylpyridin-4-yl, 2-methoxycarbonylpyridin-5-yl, 2,6-dimethyl-3-carbamoylpyridin-5-yl, indol-2-yl, 5-carboxypyrrol-2-yl, 6-carboxypyridin-2-yl, 6-ethoxycarbonylpyridin-2-yl, 5-carboxyfuran-2-yl, 6-hydroxymethylyridin-2-yl, 2-carboxy-4-methylpyridin-6-yl, 5-carboxythiophen-2-yl, 4-ethoxycarbonylthiazol-2-yl, 4-carboxylthiazol-2-yl, 4-carboxy-5-methylthiazol-2-yl, 3-carboxypyridin-5-yl, 4-carboxypyridin-2-yl, 5-carboxypyridin-2-yl, 3-carboxypyridin-2-yl, 2-carboxypyridin-4-yl, 2-carboxypyridin-5-yl, 2-methyl-3-carboxypyridin-5-yl, 2,6-dimethyl-3-carboxypyridin-5-yl, 4-methyl-5-methoxycarbonylthiazol-2-yl, 5-carboxypyridmidin-2-yl, 6-carboxypyrazin-2-yl, 4-carboxypyrrol-2-yl, 4-carboxyfuran-2-yl, 5-carboxyfuran-3-yl, 4-carboxythiophen-3-yl, 5-carboxythiophen-3-yl, 5-carboxythiazol-2-yl, 4-methyl-6-hydroxymethylpyridin-2-yl-N-oxide, 2-methylpyridin-2-yl-N-oxide, pyridin-4-yl-N-oxide, 6-chloropyridin-2-yl, pyridin-2-yl-N-oxide, 4-carboxy-6-ethoxycarbonylpyridin-2-yl, pyrazin-2-yl-4-oxide, pyrazin-2-yl-1,4-dioxide, pyrimidin-2-yl-1-oxide, 2-acetamido-3-carboxythiophen-5-yl, 3-acetylpyrid-2-yl, 2-amino-3-ethoxycarbonylthiophen-5-yl, 2-amino-4-methylpyrimid-5-yl, 4-aminopyrid-3-yl, 5-cyano-4-hydroxy-2-methylpyrid-3-yl, 5-ethoxycarbonyl-2-hydroxy-4-methylpyrid-3-yl, 3-ethoxycarbonyl-5-methylisoxazol-4-yl, 3-ethoxycarbonylisoxazol-5-yl, 2-methylaminothiazol-5-yl, 3-methylpyridin-2-yl, 4-methylpyridin-2-yl, 2-methylpyrimidin-4-yl, 5-hydroxypyridin-2-yl, 3-chloropyridin-4-yl, pyrazin-2-yl, 2-pyridyl, 3-pyridyl, 4-pyridyl, 6-ethoxycarbonyl-5-hydroxypyridin-2-yl, pyrimidin-2-yl, 6-carboxy-5-hydroxypyridin-2-yl, 6-hydroxymethyl-4-methylpyridin-2-yl, 2-methylpyridin-4-yl, 2-cyanopyridin-4-yl, 2-acetoxypyridin-4-yl, 3-nitro-6-methoxycarbonylpyridin-2-yl, 3-acetyl-4-ethoxycarbonylpyridin-5-yl, 2-methoxy-3,4-dimethoxycarbonylpyridin-6-yl, 2-furyl, 4-chloropyridin-2-yl, 2-hydroxymethylpyridin-4-yl, 3-methoxycarbonylpyridin-2-yl, 5-ethoxycarbonylimidazol-2-yl, 5-carboxypyrazin-2-yl, 4-carboxypyrimidin-2-yl, 5-carboxyimidazol-2-yl, 4-fluoro-6-carboxypyridin-2-yl, 4-methoxy-6-carboxypyridin-2-yl, 4-hydroxy-6-carboxypyridin-2-yl, 4-amino-6-carboxypyridin-2-yl, 4-dimethylamino-6-carboxypyridin-2-yl, 4,6-dicarboxypyridin-2-yl, 3-carboxypyrazin-2-yl, 3-cyanopyrazin-2-yl, 5-cyanopyrazin-2-yl, 6-cyanopyrimidin-2-yl, 6-cyanopyridin-2-yl and 3-carboxy-4-hydroxy-7-chloroquinolin-2-yl.

Suitable salts of compounds of the formula I—depending on substitution—are all acid addition salts or all salts with bases. Particular mention may be made of the pharmacologically tolerable salts of the inorganic and organic acids and bases customarily used in pharmacy. Those suitable are, on the one hand, water-soluble and water-insoluble acid addition salts with acids, such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, the acids being employed in salt preparation—depending on whether it is a mono- or polybasic acid and depending on which salt is desired—in an equimolar quantitative ratio or one differing therefrom.

On the other hand, salts with bases are also suitable. Examples of salts with bases which may be mentioned are alkali metal (lithium, sodium, potassium) or calcium, aluminum, magnesium, titanium, ammonium, meglumine or guanidinium salts, where here too the bases are employed in salt preparation in an equimolar quantitative ratio or one differing therefrom.

Pharmacologically intolerable salts, which can be initially obtained, for example, as process products in the preparation of the compounds according to the invention on an industrial scale, are converted into pharmacologically tolerable salts by processes known to the person skilled in the art.

Compounds of the formula I to be emphasized are those in which

R1 is 1-4C-alkoxy, 3-5C-cycloalkoxy, 3-5C-cycloalkylmethoxy or 1-4C-alkoxy which is completely or mainly substituted by fluorine, R2 is 1-4C-alkyl and R3 is hydrogen or 1-4C-alkyl, or R2 and R3, together and including the two carbon atoms to which they are bonded, are a cyclopentane, cyclohexane, tetrahydrofuran or tetrahydropyran ring, R4 is a phenyl ring substituted by R41 and R42 or a mono- or bicyclic heterocycle substituted by R44 and R45, which is selected from the group consisting of pyridine, pyrrole, quinoline, isoquinoline, indole, isoindole, indolizine, pyrimidine, pyrazine, pyridazine, pyrazole, imidazole, quinoxaline, quinazoline, cinnoline, benzimidazole, oxazole, isoxazole, thiazole and isothiazole, where R41 is hydrogen, carboxyl, 1-4C-alkoxycarbonyl, carbamoyl, hydroxysulfonyl, sulfamoyl, mono- or di-1-4C-alkylaminocarbonyl, mono- or di-1-4C-alkylaminosulfonyl, amino, mono- or di-1-4C-alkylamino, 1-4C-alkylcarbonylamino, 1-4C-alkylsulfonyl, 1-4C-alkoxysulfonyl, hydroxy-1-4C-alkyl, hydroxyl, 1-4C-alkoxy, 1-4C-alkyl, 1-4C-alkylcarbonyl, 1-4C-alkylcarbonyloxy, halogen, cyano or nitro, R42 is hydrogen, hydroxyl, nitro, halogen, 1-4C-alkoxycarbonyl, 1-4C-alkylcarbonyloxy, 1-4C-alkylcarbonyl, carboxyl or 1-4C-alkoxy, R44 is hydrogen, carboxyl, 1-4C-alkoxycarbonyl, carbamoyl, hydroxysulfonyl, sulfamoyl, mono- or di-1-4C-alkylaminocarbonyl, mono- or di-1-4C-alkylaminosulfonyl, amino, mono- or di-1-4C-alkylamino, 1-4C-alkylcarbonylamino, hydroxy-1-4C-alkyl, hydroxyl, 1-4C-alkoxy, 1-4C-alkyl, 1-4C-alkylcarbonyl, halogen or cyano and R45 is hydrogen, hydroxyl, halogen, carboxyl, amino, 1-4C-alkyl or 1-4C-alkoxy, R5 is hydrogen or halogen, n is 0 or 1, the salts of these compounds and the N-oxides of the pyridines, quinolines, isoquinolines, pyrimidines, pyrazines, imidazoles, quinoxalines, quinazolines and benzimidazoles and their salts.

Compounds of the formula I to be particularly emphasized are those in which

R1 is 1-4C-alkoxy, 3-5C-cycloalkoxy or 1-2C-alkoxy which is completely or mainly substituted by fluorine, R2 and R3, together and including the two carbon atoms to which they are bonded, are a cyclopentane or cyclohexane ring, R4 is a phenyl ring substituted by R41 and R42 or a mono- or bicyclic heterocycle substituted by R44 and R45, which is selected from the group consisting of pyridine, pyrrole, quinoline, isoquinoline, indole, isoindole and indolizine, where R41 is hydrogen, carboxyl, 1-4C-alkoxycarbonyl, carbamoyl, hydroxysulfonyl, sulfamoyl, mono- or di-1-4C-alkylaminocarbonyl, mono- or di-1-4C-alkylaminosulfonyl, amino, mono- or di-1-4C-alkylamino, 1-4C-alkylcarbonylamino, 1-4C-alkylsulfonyl, 1-4C-alkoxysulfonyl, hydroxy-1-4C-alkyl, hydroxyl, 1-4C-alkoxy, 1-4C-alkyl, 1-4C-alkylcarbonyl, 1-4C-alkylcarbonyloxy, halogen, cyano or nitro, R42 is hydrogen, hydroxyl, nitro, halogen, 1-4C-alkoxycarbonyl, 1-4C-alkylcarbonyloxy, 1-4C-alkylcarbonyl, carboxyl or 1-4C-alkoxy, R44 is hydrogen, carboxyl, 1-4C-alkoxycarbonyl, carbamoyl, hydroxysulfonyl, sulfamoyl, mono- or di-1-4C-alkylaminocarbonyl, mono- or di-1-4C-alkylaminosulfonyl, amino, mono- or di-1-4C-alkylamino, 1-4C-alkylcarbonylamino, hydroxy-1-4C- alkyl, hydroxyl, 1-4C-alkoxy, 1-4C-alkyl, 1-4C-alkylcarbonyl, halogen or cyano and R45 is hydrogen, hydroxyl, halogen, carboxyl, amino, 1-4C-alkyl or 1-4C-alkoxy, R5 is hydrogen, n is 0, the salts of these compounds and the N-oxides of the pyridines and their salts.

Preferred compounds of the formula I are those in which

R1 is 1-4C-alkoxy or 1-2C-alkoxy which is completely or mainly substituted by fluorine, R2 and R3, together and including the two carbon atoms to which they are bonded, are a cyclopentane ring, R4 is a phenyl ring substituted by R41 and R42 or pyridine substituted by R44 and R45, where R41 is hydrogen, carboxyl, 1-4C-alkoxycarbonyl, carbamoyl, hydroxysulfonyl, sulfamoyl, mono- or di-1-4C-alkylaminocarbonyl, mono- or di-1-4C-alkylaminosulfonyl, amino, mono- or di-1-4C-alkylamino, 1-4C-alkylcarbonylamino, 1-4C-alkylsulfonyl, 1-4C-alkoxysulfonyl, hydroxy-1-4C-alkyl, hydroxyl, 1-4C-alkoxy, 1-4C-alkyl, 1-4C-alkylcarbonyl, 1-4C-alkylcarbonyloxy, halogen, cyano or nitro, R42 is hydrogen, hydroxyl, nitro, halogen, 1-4C-alkoxycarbonyl, 1-4C-alkylcarbonyloxy, 1-4C-alkylcarbonyl, carboxyl or 1-4C-alkoxy, R44 is hydrogen, carboxyl, 1-4C-alkoxycarbonyl, carbamoyl, hydroxysulfonyl, sulfamoyl, mono- or di-1-4C-alkylaminocarbonyl, mono- or di-1-4C-alkylaminosulfonyl, amino, mono- or di-1-4C-alkylamino, 1-4C-alkylcarbonylamino, hydroxy-1-4C-alkyl, hydroxyl, 1-4C-alkoxy, 1-4C-alkyl, 1-4C-alkylcarbonyl, halogen or cyano and R45 is hydrogen, hydroxyl, halogen, carboxyl, amino, 1-4C-alkyl or 1-4C-alkoxy, R5 is hydrogen, n is 0, the salts of these compounds and the N-oxides of the pyridines and their salts.

Particularly preferred compounds of the formula I are those in which

R1 is 1-4C-alkoxy,

R2 and R3, together and including the two carbon atoms to which they are bonded, are a cyclopentane ring, R4 is a phenyl ring substituted by R41 or pyridine substituted by R44, where R41 is hydrogen, carboxyl, 1-4C-alkoxycarbonyl, carbamoyl, hydroxysulfonyl, sulfamoyl or hydroxyl and R44 is hydrogen, carboxyl, 1-4C-alkoxycarbonyl, carbamoyl, hydroxysulfonyl, sulfamoyl or hydroxyl, R5 is hydrogen, n is 0, and the salts of these compounds.

Particularly preferred compounds of the formula I to be emphasized are those in which R1 is methoxy, R2 and R3, together and including the two carbon atoms to which they are bonded, are a cyclopentane ring, R4 is a phenyl ring substituted by R41 or pyridine substituted by R44, where R41 is carboxyl or carbamoyl and R44 is hydrogen, carboxyl or 1-4C-alkoxycarbonyl, R5 is hydrogen, n is 0, and the salts of these compounds.

Exemplary compounds according to the invention are listed in the following tables:

TABLE 1

Compounds of the formula I with R4 = 3-pyridyl, 4-pyridyl, 5-carboxypyrid-3-yl, 5-carbamoylpyrid-3-yl or 5-methoxycarbonylpyrid-3-yl, R5 = H, n = 0 and the following further substituent meanings:

| R1 | R2 | R3 |
|---|---|---|
| $OCH_3$ | $CH_3$ | H |
| $OC_2H_5$ | $CH_3$ | H |
| $OCH_2C_3H_5$ | $CH_3$ | H |
| $OCF_2H$ | $CH_3$ | H |
| $OCF_3$ | $CH_3$ | H |
| $OCH_2CF_3$ | $CH_3$ | H |
| $OCH_3$ | $C_2H_5$ | $CH_3$ |
| $OC_2H_5$ | $C_2H_5$ | $CH_3$ |
| $OCH_2C_3H_5$ | $C_2H_5$ | $CH_3$ |
| $OCF_2H$ | $C_2H_5$ | $CH_3$ |
| $OCF_3$ | $C_2H_5$ | $CH_3$ |
| $OCH_2CF_3$ | $C_2H_5$ | $CH_3$ |
| $OCH_3$ | $CH_2CH_2CH_2$ | |
| $OC_2H_5$ | $CH_2CH_2CH_2$ | |
| $OCH_2C_3H_5$ | $CH_2CH_2CH_2$ | |
| $OCF_2H$ | $CH_2CH_2CH_2$ | |
| $OCF_3$ | $CH_2CH_2CH_2$ | |
| $OCH_2CF_3$ | $CH_2CH_2CH_2$ | |
| $OCH_3$ | $CH_2CH_2CH_2CH_2$ | |
| $OC_2H_5$ | $CH_2CH_2CH_2CH_2$ | |
| $OCH_2C_3H_5$ | $CH_2CH_2CH_2CH_2$ | |
| $OCF_2H$ | $CH_2CH_2CH_2CH_2$ | |
| $OCF_3$ | $CH_2CH_2CH_2CH_2$ | |
| $OCH_2CF_3$ | $CH_2CH_2CH_2CH_2$ | |
| $OCH_3$ | $CH_2-O-CH_2$ | |
| $OC_2H_5$ | $CH_2-O-CH_2$ | |
| $OCH_2C_3H_5$ | $CH_2-O-CH_2$ | |
| $OCF_2H$ | $CH_2-O-CH_2$ | |
| $OCF_3$ | $CH_2-O-CH_2$ | |
| $OCH_2CF_3$ | $CH_2-O-CH_2$ | |
| $OCH_3$ | $CH_2CH_2-O$ | |
| $OC_2H_5$ | $CH_2CH_2-O$ | |
| $OCH_2C_3H_5$ | $CH_2CH_2-O$ | |
| $OCF_2H$ | $CH_2CH_2-O$ | |
| $OCF_3$ | $CH_2CH_2-O$ | |
| $OCH_2CF_3$ | $CH_2CH_2-O$ | |
| $OCH_3$ | $CH_2CH_2-O-CH_2$ | |
| $OC_2H_5$ | $CH_2CH_2-O-CH_2$ | |
| $OCH_2C_3H_5$ | $CH_2CH_2-O-CH_2$ | |
| $OCF_2H$ | $CH_2CH_2-O-CH_2$ | |
| $OCF_3$ | $CH_2CH_2-O-CH_2$ | |
| $OCH_2CF_3$ | $CH_2CH_2-O-CH_2$ | |

TABLE 2

Compounds of the formula I with R4 = 3-pyridyl, 4-pyridyl, 5-carboxypyrid-3-yl, 5-carbamoylpyrid-3-yl or 5-methoxycarbonylpyrid-3-yl, R5 = H, n = 1 and the following further substituent meanings:

| R1 | R2 | R3 |
|---|---|---|
| $OCH_3$ | $CH_3$ | H |
| $OC_2H_5$ | $CH_3$ | H |
| $OCH_2C_3H_5$ | $CH_3$ | H |
| $OCF_2H$ | $CH_3$ | H |
| $OCF_3$ | $CH_3$ | H |
| $OCH_2CF_3$ | $CH_3$ | H |
| $OCH_3$ | $C_2H_5$ | $CH_3$ |
| $OC_2H_5$ | $C_2H_5$ | $CH_3$ |
| $OCH_2C_3H_5$ | $C_2H_5$ | $CH_3$ |
| $OCF_2H$ | $C_2H_5$ | $OH_3$ |
| $OCF_3$ | $C_2H_5$ | $CH_3$ |
| $OCH_2CF_3$ | $C_2H_5$ | $CH_3$ |
| $OCH_3$ | $CH_2CH_2CH_2$ | |
| $OC_2H_5$ | $CH_2CH_2CH_2$ | |
| $OCH_2C_3H_5$ | $CH_2CH_2CH_2$ | |
| $OCF_2H$ | $CH_2CH_2CH_2$ | |
| $OCF_3$ | $CH_2CH_2CH_2$ | |

TABLE 2-continued

Compounds of the formula I with R4 = 3-pyridyl, 4-pyridyl, 5-carboxypyrid-3-yl, 5-carbamoylpyrid-3-yl or 5-methoxycarbonylpyrid-3-yl, R5 = H, n = 1 and the following further substituent meanings:

| R1 | R2 | R3 |
|---|---|---|
| $OCH_2CF_3$ | $CH_2CH_2CH_2$ | |
| $OCH_3$ | $CH_2CH_2CH_2CH_2$ | |
| $OC_2H_5$ | $CH_2CH_2CH_2CH_2$ | |
| $OCH_2C_3H_5$ | $CH_2CH_2CH_2CH_2$ | |
| $OCF_2H$ | $CH_2CH_2CH_2CH_2$ | |
| $OCF_3$ | $CH_2CH_2CH_2CH_2$ | |
| $OCH_2CF_3$ | $CH_2CH_2CH_2CH_2$ | |
| $OCH_3$ | $CH_2-O-CH_2$ | |
| $OC_2H_5$ | $CH_2-O-CH_2$ | |
| $OCH_2C_3H_5$ | $CH_2-O-CH_2$ | |
| $OCF_2H$ | $CH_2-O-CH_2$ | |
| $OCF_3$ | $CH_2-O-CH_2$ | |
| $OCH_2CF_3$ | $CH_2-O-CH_2$ | |
| $OCH_3$ | $CH_2CH_2-O$ | |
| $OC_2H_5$ | $CH_2CH_2-O$ | |
| $OCH_2C_3H_5$ | $CH_2CH_2-O$ | |
| $OCF_2H$ | $CH_2CH_2-O$ | |
| $OCF_3$ | $CH_2CH_2-O$ | |
| $OCH_2CF_3$ | $CH_2CH_2-O$ | |
| $OCH_3$ | $CH_2CH_2-O-CH_2$ | |
| $OC_2H_5$ | $CH_2CH_2-O-CH_2$ | |
| $OCH_2C_3H_5$ | $CH_2CH_2-O-CH_2$ | |
| $OCF_2H$ | $CH_2CH_2-O-CH_2$ | |
| $OCF_3$ | $CH_2CH_2-O-CH_2$ | |
| $OCH_2CF_3$ | $CH_2CH_2-O-CH_2$ | |

TABLE 3

Compounds of the formula I with R4 = phenyl, 3-carboxyphenyl, 4-carboxyphenyl, 3-carbamoylphehyl or 4-carbamoylphenyl, R5 = H, n = 0 and the following further substituent meanings:

| R1 | R2 | R3 |
|---|---|---|
| $OCH_3$ | $CH_3$ | H |
| $OC_2H_5$ | $CH_3$ | H |
| $OCH_2C_3H_5$ | $CH_3$ | H |
| $OCF_2H$ | $CH_3$ | H |
| $OCF_3$ | $CH_3$ | H |
| $OCH_2CF_3$ | $CH_3$ | H |
| $OCH_3$ | $C_2H_5$ | $CH_3$ |
| $OC_2H_5$ | $C_2H_5$ | $CH_3$ |
| $OCH_2C_3H_5$ | $C_2H_5$ | $CH_3$ |
| $OCF_2H$ | $C_2H_5$ | $CH_3$ |
| $OCF_3$ | $C_2H_5$ | $CH_3$ |
| $OCH_2CF_3$ | $C_2H_5$ | $CH_3$ |
| $OCH_3$ | | $CH_2CH_2CH_2$ |
| $OC_2H_5$ | | $CH_2CH_2CH_2$ |
| $OCH_2C_3H_5$ | | $CH_2CH_2CH_2$ |
| $OCF_2H$ | | $CH_2CH_2CH_2$ |
| $OCF_3$ | | $CH_2CH_2CH_2$ |
| $OCH_2CF_3$ | | $CH_2CH_2CH_2$ |
| $OCH_3$ | | $CH_2CH_2CH_2CH_2$ |
| $OC_2H_5$ | | $CH_2CH_2CH_2CH_2$ |
| $OCH_2C_3H_5$ | | $CH_2CH_2CH_2CH_2$ |
| $OCF_2H$ | | $CH_2CH_2CH_2CH_2$ |
| $OCF_3$ | | $CH_2CH_2CH_2CH_2$ |
| $OCH_2CF_3$ | | $CH_2CH_2CH_2CH_2$ |
| $OCH_3$ | | $CH_2-O-CH_2$ |
| $OC_2H_5$ | | $CH_2-O-CH_2$ |
| $OCH_2C_3H_5$ | | $CH_2-O-CH_2$ |
| $OCF_2H$ | | $CH_2-O-CH_2$ |
| $OCF_3$ | | $CH_2-O-CH_2$ |
| $OCH_2CF_3$ | | $CH_2-O-CH_2$ |
| $OCH_3$ | | $CH_2CH_2-O$ |
| $OC_2H_5$ | | $CH_2CH_2-O$ |
| $OCH_2C_3H_5$ | | $CH_2CH_2-O$ |
| $OCF_2H$ | | $CH_2CH_2-O$ |
| $OCF_3$ | | $CH_2CH_2-O$ |
| $OCH_2CF_3$ | | $CH_2CH_2-O$ |
| $OCH_3$ | | $CH_2CH_2-O$ |
| $OC_2H_5$ | | $CH_2CH_2-O$ |
| $OCH_2C_3H_5$ | | $CH_2CH_2-O$ |
| $OCF_2H$ | | $CH_2CH_2-O$ |
| $OCF_3$ | | $CH_2CH_2-O$ |
| $OCH_2CF_3$ | | $CH_2CH_2-O$ |
| $OCH_3$ | | $CH_2CH_2-O-CH_2$ |
| $OC_2H_5$ | | $CH_2CH_2-O-CH_2$ |
| $OCH_2C_3H_5$ | | $CH_2CH_2-O-CH_2$ |
| $OCF_2H$ | | $CH_2CH_2-O-CH_2$ |
| $OCF_3$ | | $CH_2CH_2-O-CH_2$ |
| $OCH_2CF_3$ | | $CH_2CH_2-O-CH_2$ |

TABLE 4

Compounds of the formula I with R4 = phenyl, 3-carboxyphenyl, 4-carboxyphenyl, 3-carbamoylphenyl or 4-carbamoylphenyl, R5 = H, n = 1 and the following further substituent meanings:

| R1 | R2 | R3 |
|---|---|---|
| $OCH_3$ | $CH_3$ | H |
| $OC_2H_5$ | $CH_3$ | H |
| $OCH_2C_3H_5$ | $CH_3$ | H |
| $OCF_2H$ | $CH_3$ | H |
| $OCF_3$ | $CH_3$ | H |
| $OCH_2CF_3$ | $CH_3$ | H |
| $OCH_3$ | $C_2H_5$ | $CH_3$ |
| $OC_2H_5$ | $C_2H_5$ | $CH_3$ |
| $OCH_2C_3H_5$ | $C_2H_5$ | $CH_3$ |
| $OCF_2H$ | $C_2H_5$ | $CH_3$ |
| $OCF_3$ | $C_2H_5$ | $CH_3$ |
| $OCH_2CF_3$ | $C_2H_5$ | $CH_3$ |
| $OCH_3$ | | $CH_2CH_2CH_2$ |
| $OC_2H_5$ | | $CH_2CH_2CH_2$ |
| $OCH_2C_3H_5$ | | $CH_2CH_2CH_2$ |
| $OCF_2H$ | | $CH_2CH_2CH_2$ |
| $OCF_3$ | | $CH_2CH_2CH_2$ |
| $OCH_2CF_3$ | | $CH_2CH_2CH_2$ |
| $OCH_3$ | | $CH_2CH_2CH_2CH_2$ |
| $OC_2H_5$ | | $CH_2CH_2CH_2CH_2$ |
| $OCH_2C_3H_5$ | | $CH_2CH_2CH_2CH_2$ |
| $OCF_2H$ | | $CH_2CH_2CH_2CH_2$ |
| $OCF_3$ | | $CH_2CH_2CH_2CH_2$ |
| $OCH_2CF_3$ | | $CH_2CH_2CH_2CH_2$ |
| $OCH_3$ | | $CH_2-O-CH_2$ |
| $OC_2H_5$ | | $CH_2-O-CH_2$ |
| $OCH_2C_3H_5$ | | $CH_2-O-CH_2$ |
| $OCF_2H$ | | $CH_2-O-CH_2$ |
| $OCF_3$ | | $CH_2-O-CH_2$ |
| $OCH_2CF_3$ | | $CH_2-O-CH_2$ |
| $OCH_3$ | | $CH_2CH_2-O$ |
| $OC_2H_5$ | | $CH_2CH_2-O$ |
| $OCH_2C_3H_5$ | | $CH_2CH_2-O$ |
| $OCF_2H$ | | $CH_2CH_2-O$ |
| $OCF_3$ | | $CH_2CH_2-O$ |
| $OCH_2CF_3$ | | $CH_2CH_2-O$ |
| $OCH_3$ | | $CH_2CH_2-O-CH_2$ |
| $OC_2H_5$ | | $CH_2CH_2-O-CH_2$ |
| $OCH_2C_3H_5$ | | $CH_2CH_2-O-CH_2$ |
| $OCF_2H$ | | $CH_2CH_2-O-CH_2$ |
| $OCF_3$ | | $CH_2CH_2-O-CH_2$ |
| $OCH_2CF_3$ | | $CH_2CH_2-O-CH_2$ |

The compounds of the formula I—if the substituents —R2 and $CH_2R3$ are not identical—are chiral compounds. The invention therefore includes both the pure enantiomers and also their mixtures in any mixing ratio, including the racemates. The enantiomers can be separated in a manner known per se (for example by preparation and separation of corresponding diestereoisomeric compounds).

The invention further relates to a process for the preparation of the compounds of the formula I and their salts. The process comprises reacting compounds of the formula II, in which R1, R2 and R3 have the meanings indicated above and Z is the group —C(S)—NH$_2$, with compounds of the formula III, in which R4, R5 and n have the meanings indicated above and Y is a suitable leaving group, and, if desired, then converting compounds of the formula I obtained into their salts or, if desired, then converting salts of the compounds of the formula I obtained into the free compounds.

The person skilled in the art is familiar on the basis of his/her expert knowledge with the leaving groups Y which are suitable. For example, starting materials used are suitable compounds of the formula III in which Y has the meaning halogen, in particular bromine or chlorine. Otherwise, the reaction is carried out in a manner familiar per se to the person skilled in the art (e.g. as described in EP 0 513 387 and EP 0 600 092) in a suitable solvent and in the presence or absence of a base, preferably at reaction temperatures of between room temperature and the boiling temperature of the solvent used and with reaction times between one hour and two days. Suitable solvents are, for example, alcohols, such as methanol, ethanol or propanol, cyclic hydrocarbons, such as toluene or xylene, ethers such as diethyl ether, tetrahydrofuran or dioxane, halogenated hydrocarbons, such as dichloromethane or chloroform, polar solvents such as dimethylformamide, acetonitrile or dimethyl sulfoxide or, if desired, alternatively mixtures of the solvents mentioned. Preferred bases which are used are nitrogen bases, such as triethylamine, ethyldiisopropylamine, N-methylmorpholine or pyridine. The bases can be added here in an equimolar ratio (based on compounds of the formula (III) or preferably in an excess.

If desired, compounds of the formula I obtained can also be converted into other compounds of the formula I by use of methods known to the person skilled in the art. The preparation of carboxamides of the formula I from the corresponding carboxylic acids of the formula I may be mentioned by way of example. To this end, the carboxylic acids of the formula I are reacted with suitable amines in a manner which is known to the person skilled in the art for the synthesis of carboxamides. If desired, the carboxylic acid of the formula I is converted into a suitably activated derivative, for example an appropriate acid halide, before the aminolysis. For example, ammonia, methylamine or ethylamine may be mentioned as suitable amines which can be employed.

The preparation of carboxylic acids of the formula I from corresponding esters of the formula I, for example by hydrolysis in a manner known to the person skilled in the art, for example as described in the examples, may also be mentioned by way of example.

If desired, quinolines, isoquinolines, pyrimidines, pyrazines, imidazoles, quinoxalines, quinazolines, benzimidazoles and in particular pyridines of the formula I obtained can also be converted into the corresponding N-oxides or their salts.

The N-oxidation is carried out in a manner which is likewise familiar to the person skilled in the art, for example with the aid of m-chloroperoxybenzoic acid in dichloromethane at room temperature. The person skilled in the art is familiar on the basis of his/her expert knowledge with the reaction conditions which are specifically necessary for carrying out the process.

The substances according to the invention are isolated and purified in a manner known per se, for example by distilling off the solvent in vacuo and recrystallizing the residue obtained from a suitable solvent or subjecting it to one of the customary purification methods, such as, for example, column chromatography on suitable support material.

Salts are obtained by dissolving the free compound in a suitable solvent, e.g. in a chlorinated hydrocarbon, such as methylene chloride or chloroform, or a low molecular weight aliphatic alcohol (ethanol, isopropanol) which contains the desired acid or base, or to which the desired acid or base is then added. The salts are obtained by filtering, reprecipitating, preciptating with a nonsolvent for the addition salt or by evaporating the solvent. Salts obtained can be converted by alkalization or by acidification into the free compounds, which in turn can be converted into salts. In this manner, pharmacologically intolerable salts can be converted into pharmacologically tolerable salts.

The compounds of the formula II in which Z is the group —C(S)—NH$_2$ can be prepared in a manner familiar to the person skilled in the art, for example by addition of hydrogen sulfide to compounds of the formula II, in which Z is a nitrile group (—CN) [e.g. as described in W. Christ, D. Rakow, S. Strauss, J. Heterocycl. Chem. 11, 397 (1974)].

The compounds of the formula II in which Z is a nitrile group can be prepared as described in the literature (T. Savaie, T. Ishiguro, K. Kawashima, K. Morita; Tetrahedron Lett. 1973, 2121–2124) from the corresponding compounds of the formula II in which Z has the meaning carbamoyl [—C(O)—NH$_2$].

The compounds of the formula II in which Z has the meaning carbamoyl can be prepared from the compounds of the formula II in which Z has the meaning carboxyl in a manner familiar to the person skilled in the art, for example as described in the following examples.

Compounds of the formula II in which Z is carboxyl are either known from the International Patent Application WO96/03399 or can be prepared in an analogous manner.

The compounds of the formula III in which R4 and R5 have the meanings indicated above, n=0 and Y is halogen, in particular chlorine or bromine, are either known (e.g. from EP 0 513 387 and EP 0 600 092) or can be obtained in a known manner, for example by chlorination or bromination of corresponding compounds of the formula III in which Y has the meaning hydrogen.

The compounds of the formula III in which R4 and R5 have the meanings indicated above, n=1 or 2 and Y is halogen, in particular chlorine or bromine, are either known or can be obtained with the aid of methods which are familiar to the person skilled in the art and described in the technical literature, for example by reaction of compounds of the formula R4—(CH$_2$)n—Mg—L, in which R4 has the meanings indicated above, n=1 or 2 and L is halogen, in particular bromine, with compounds of the formula IV, in which R5 has the meanings indicated above, Y is a suitable leaving group (in particular chlorine or bromine) and X is a suitable leaving group (in particular chlorine or bromine).

Compounds of the formula R4—(CH$_2$)n—Mg—L, in which n=1 or 2, are accessible from corresponding compounds of the formula R4—(CH$_2$)n—L by reaction with magnesium.

Alternatively, compounds of the formula III in which R4 and n have the meanings indicated above, R5 is hydrogen and Y is in particular chlorine or bromine can also be obtained by reaction of compounds of the formula IIIa in which R4 and n have the meanings indicated above and A is a suitable leaving group, in particular chlorine or bromine, with diazomethane and subsequent treatment with HCl or HBr.

The compounds of the formula III in which R5 has the meanings indicated above, R4 is one of the abovementioned heterocycles substituted by R44, R45 and R46, or by R44 and R45, in particular pyridine, n=1 and Y is halogen, in particular chlorine or bromine, can be obtained, for example, by reaction of corresponding compounds of the formula M—CH$_2$—R4, in which M is a suitable metal atom, for example lithium, with compounds of the formula IV, in which R5 has the meanings mentioned above, Y is a suitable leaving group, in particular chlorine or bromine, and X is a suitable leaving group, for example halogen (in particular chlorine or bromine) or 1-4C-alkoxy (in particular methoxy or ethoxy). The reaction is otherwise carried out in a manner familiar to the person skilled in the art, for example as described in the following examples.

Compounds of the formula M—CH$_2$—R4, in which M has the meaning lithium, are accessible, for example, by reaction of suitable compounds of the formula H$_3$C—R4 with an alkyllithium compound, for example butyllithium, under customary reaction conditions. The compounds mentioned in the examples and their salts are a preferred subject of the invention.

The following examples explain the invention in greater detail, without restricting it. Further compounds of the formula I whose preparation is not explicitly described can also be prepared in an analogous manner or in a manner which is familiar per se to the person skilled in the art using customary process techniques.

In the examples, m.p. stands for melting point, h for hour(s), RT for room temperature, min. for minute(s), tol. for toluene, EA for ethyl acetate and PE for petroleum ether. The compounds mentioned in the examples and their salts are a preferred subject of the invention.

EXAMPLES

Final Products

1. 3-[2-(2,3-Dihydro-7-methoxybenzofuran-2-spiro-1'-cyclopentan-4-yl)thiazol-4-yl]pyridine 260 mg (1.0 mmol) of 2,3-dihydro-7-methoxybenzofuran-2-spiro-1'-cyclopentan-4-yl-thiocarboxamide and 340 mg (1.2 mmol) of 2-bromo-1-(pyridin-3-yl)ethanone hydrobromide are stirred at RT for 4 h in 30 ml of ethanol. The mixture is concentrated in vacuo, the residue is suspended in H$_2$O, and the mixture is rendered alkaline and extracted with ethyl acetate. The organic phase is dried over MgSO$_4$, evaporated and the solid residue is recrystallized from 10 ml of ethanol. 176 mg (48%) of the title compound of m.p. 160–162° C. are obtained.

2. 4-[2-(2,3-Dihydro-7-methoxybenzofuran-2-spiro-1'-cyclopentan-4-yl)thiazol-4-yl]pyridinehydrobromide 500 mg (1.9 mmol) of 2,3-dihydro-7-methoxybenzofuran-2-spiro-1'-cyclopentan-4-yl-thiocarboxamide and 533 mg (1.9 mmol) of 2-bromo-1-(pyridin-4-yl)ethanone hydrobromide are stirred at 40° C. for 4 h in 20 ml of ethanol. The precipitate is filtered off with suction and washed with ethanol and 630 mg (91%) of the title compound of m.p. 205–207° C. are obtained.

3. 3-[2-(2,3-Dihydro-7-methoxybenzofuran-2-spiro-1'-cyclopentan-4-yl)thiazol-4-yl]pyridine-5-carboxylate hydrobromide 1.47 g (5.59 mmol) of 2,3-dihydro-7-methoxybenzofuran-2-spiro-1'-cyclopentan-4-ylthiocarboxamide and 1.45 g (5.59 mmol) of methyl 5-bromoacetyl-nicotinate are stirred at 70° C. for 1.5 h in 30 ml of ethanol. The resulting precipitate is filtered off with suction, recrystallized in diisopropyl ether and 1.38 g (48%) of the title compound of m.p. 211° C. are obtained.

4. 3-[2-(2,3-Dihydro-7-methoxybenzofuran-2-spiro-1'-cyclopentan-4-yl)thiazol-4-yl]pyridine-5-carboxylic acid 1.20 g (2.84 mmol) of the compound 3 and 312 mg (13.05 mmol) of lithium hydroxide are suspended in a mixture of methanol and water. After stirring at 40° C. for 3 h, the reaction solution, which by now is clear, is neutralized with 2N HCl and concentrated. The residue is partitioned between ethyl acetate and water. The organic phase contains both dissolved and undissolved product. The solid is filtered off, and the solution is dried over MgSO$_4$ and concentrated. The combined crude product is stirred in ethanol and 1.03 g (89%) of the title compound of m.p.>270° C. are obtained.

5. 3-[2-(2,3-Dihydro-7-methoxybenzofuran-2-spiro-1'-cyclopentan-4-yl)thiazol-4-yl]benzoic acid 260 mg (1.0 mmol) of 2,3-dihydro-7-methoxybenzofuran-2-spiro-1'-cyclopentan-4-yl-thiocarboxamide and 360 mg of 3-bromoacetylbenzoic acid are stirred at RT for 2 h with addition of 0.5 ml of triethylamine in 20 ml of ethanol. The mixture is concentrated, the residue is suspended in H$_2$O and the mixture is acidified with conc. HCl. After extraction a number of times with ethyl acetate, the combined organic phases are dried over MgSO$_4$ and concentrated. The residue is extracted by boiling with 15 ml of ethanol and 180 mg (44%) of the title compound of m.p. 256–259° C. are obtained.

6. 3-[2-(2,3-Dihydro-7-methoxybenzofuran-2-spiro-1'-cyclopentan-4-yl)thiazol-4-yl]benzamide 800 mg (1.96 mmol) of the compound 5 are heated to reflux for 1 h in 10 ml of thionyl chloride. Excess thionyl chloride is distilled off in vacuo and the residue is shaken for 1 h in 30 ml of ice-cooled concentrated ammonia. The mixture is extracted with dichloromethane and chromatographed on silica gel (ethyl acetate). After recrystallizing twice from i-butyl methyl ketone, 60 mg (8%) of the title compound of m.p. 246° C. are obtained.

7. 4-[2-(2,3-Dihydro-7-methoxybenzofuran-2-spiro-1'-cyclopentan-4-yl)thiazol-4-yl]benzoic acid 2.0 g (7.59 mmol) of 2,3-dihydro-7-methoxybenzofuran-2-spiro-1'-cyclopentan-4-yl-thiocarboxamide and 1.84 g of 4-bromoacetyl benzoic acid are stirred at 70° C. for 40 min. in 50 ml of ethanol with addition of 768 mg (7.59 mmol) of N-methylmorpholine. After cooling the reaction solution, the precipitate is filtered off with suction, washed with ethanol and stirred with diethyl ether. 180 mg (44%) of the title compound of m.p. >250° C. are obtained.

8. 4-[2-(2,3-Dihydro-7-methoxybenzofuran-2-spiro-1'-cyclopentan-4-yl)thiazol-4-yl]benzamide 600 mg (1.47 mmol) of the compound 7 are heated to reflux for 1 h in 3 ml of thionyl chloride. Excess thionyl chloride is distilled off in vacuo and the residue is taken up in 10 ml of acetone. 10 ml of conc. ammonia are added dropwise with ice-cooling and the mixture is then stirred in an ice bath for 20 min. The precipitate is filtered off with suction and chromatographed on silica gel (Tol: EA: NEt3= 70:29:1). 100 mg (17%) of the title compound of m.p. 245° C. are obtained.

Starting Compounds

A. 2,3-Dihydro-7-methoxybenzofuran-2-spiro-1'-cyclopentan-4-ylthiocarboxamide 960 mg (4.2 mmol) of 4-cyano-2,3-dihydro-7-methoxybenzofuran-2-spiro-1'-cyclopentane are dissolved in 10 ml of triethylamine and 10 ml of pyridine. The solution is saturated with $H_2S$ and stirred at RT for 4 days. The reaction mixture is taken up in ethyl acetate and freed from the pyridine with dil. HCl. After concentration and crystallization from PE:tol.=1:1, 860 mg (78%) of the title compound of m.p. 187–190° C. are obtained.

B. 4-Cyano-2,3-dihydro-7-methoxybenzofuran-2-spiro-1'-cyclopentane 1.4 g (6.0 mmol) of 2,3-dihydro-7-methoxybenzofuran-2-spiro-1'-cyclopentanecarboxamide are dissolved in 25 ml of $CHCl_3$ and treated with 210 mg (1.0 mmol) of benzyltriethylammonium chloride. 5 ml of 50% strength NaOH are added with ice-cooling and the mixture is stirred at 15° C. for 3 h. It is treated with $H_2O$, extracted with ethyl acetate and chromatographed on silica gel (tol.). Crystallization is carried out from 5 ml of petroleum ether and 998 mg (77%) of the title compound of m.p. 74–76° C. are obtained.

C. 2,3-Dihydro-7-methoxybenzofuran-3-spiro-1'-cyclopentan-4-yl)thiazol-4-ylcarboxamide 3.5 g (14.0 nmol) of 2,3-dihydro-7-methoxybenzofuran-2-spiro-1'-cyclopentan-4-yl-carboxylic acid are treated with 10 ml (about 140 mmol) of gC. The excess $SOCl_2$ is distilled off in vacuo and the residue is taken up in 20 ml of acetone. The mixture is treated with 10 ml of conc. NH3 with ice-cooling and then stirred for 1 h. The acetone is distilled off and the residue is partitioned between ethyl acetate and 0.5 N NaOH. The dried organic phase is crystallized from 5 ml of 50% strength methanol and 115 mg (48%) of the title compound of m.p. 149–151° C. are obtained.

D. 2,3-Dihydro-7-methoxybenzofuran-2-spiro-1'-cyclopentan-4-yl carboxylic acid The preparation of the title compound is described in International Patent Application WO96/03399.

E. 2-Bromo-1-(pyridin-3-yl)ethanone hydrobromide

The preparation of the title compound is known from the literature. Ref.: A. Dornow et al., Chem. Ber. 84, 148 (1951).

F. 2-Bromo-1-(pyridin-4-yl )ethanone hydrobromide

The preparation of the title compound is known from the literature. Ref.: G. Sarodnick, G. Kempter; Pharmazie 40, 384–387 (1985).

G. Methyl 5-bromoacetylnicotinate

The preparation of the title compound is known from the literature. Ref.: S. McLean; Can. J. Chem. 54, 1262–1277 (1976)

H. 3-Bromoacetylbenzoic acid

The preparation of the title compound is known from the literature. Ref.: Schmied, Gröding, Monatshefte Chem. 84, 491, 496 (1953).

I. 4-Bromoacetylbenzoic acid

The preparation of the title compound is known from the literature. Ref.: C. Masatoshi et al.; J. Med. Chem. 38, 353–358 (1995).

Commercial Utility

The compounds according to the invention have valuable pharmacological properties which make them commercially utilizable. As selective cyclic nucleotide phosphodiesterate (PDE) inhibitors (namely of type IV), they are suitable, on the one hand, as bronchial therapeutics (for the treatment of airway obstructions on account of their dilating action but also on account of their respiratory rate- or respiratory drive-increasing action) and for the elimination of erectile dysfunction on account of the vasodilating action, but on the other hand especially for the treatment of disorders, in particular of inflammatory nature, e.g. of the airways (asthma prophylaxis), of the skin, of the intestine, of the eyes and of the joints, which are mediated by mediators such as histamine, PAF (platelet-activating factor), arachidonic acid derivatives, such as leukotrienes and prostaglandins, cytokines, interleukins, chemokines, alpha-, beta- and gamma-interferon, tumor necrosis factor (TNF) or oxygen free radicals and proteases. The compounds according to the invention are distinguished here by a low toxicity, a good enteral absorption (high bioavailability), a large therapeutic breadth and the absence of significant side effects.

On account of their PDE-inhibiting properties, the compounds according to the invention can be employed in human and veterinary medicine as therapeutics, where they can be used, for example, for the treatment and prophylaxis of the following illnesses: acute and chronic (in particular inflammatory and allergen-induced) airway disorders of various origin (bronchitis, allergic bronchitis, bronchial asthma); dermatoses (especially of proliferative, inflammatory and allergic type) such as, for example, psoriasis (vulgaris), toxic and allergic contact eczema, atopic eczema, seborrheic eczema, lichen simplex, sunburn, pruritus in the anogenital region, alopecia areata, hypertrophic scars, -diskoid lupus erythematosus, follicular and wide-area pyodermias, endogenous and exogeneous acne, acne rosacea and other proliferative, inflammatory and allergic skin disorders; disorders which are based on an excess release of TNF and leukotrienes, e.g. disorders of the arthritis type (rheumatoid arthritis, rheumatoid spondylitis, osteoarthritis and other arthritic conditions), disorders of the immune system (AIDS, multiple sclerosis), forms of shock [septic shock, endotoxin shock, gram-negative spesis, toxic shock syndrome and ARDS (adult respiratory distress syndrome)] as well as generalized inflammations in the gastrointestinal region (Crohn's disease and ulcerative colitis); disorders which are based on allergic and/or chronic, faulty immunological reactions in the region of the upper airways (pharynx, nose) and the adjacent regions (paranasal sinuses, eyes), such as, for example, allergic rhinitis/sinusitis, chronic rhinitis/sinusitis, allergic conjunctivitis and nasal polyps; but also disorders of the heart which can be treated by PDE inhibitors, such as, for example, cardiac insufficiency, or disorders which can be treated on account of the tissue-relaxant action of the PDE inhibitors, such as, for example, erectile dysfunction or colics of the kidneys and of the ureters in connection with kidney stones; or alternatively disorders of the CNS, such as, for example, depressions or arteriosclerotic dementia.

The invention further relates to a process for the treatment of mammals, including humans, who are suffering from one of the abovementioned illnesses. The process comprises administering to the sick mammal a therapeutically efficacious and pharmacologically tolerable amount of one or more of the compounds according to the invention.

The invention further relates to the compounds according to the invention for use in the treatment and/or prophylaxis of the illnesses mentioned.

The invention also relates to the use of the compounds according to the invention for the production of medicaments which are employed for the treatment and/or prophylaxis of the illnesses mentioned.

Medicaments for the treatment and/or prophylaxis of the illnesses mentioned, which contain one or more of the compounds according to the invention, are furthermore a subject of the invention.

The medicaments are prepared by processes known per se and familiar to the person skilled in the art. As medicaments, the compounds according to the invention (=active compounds) are either employed as such, or preferably in combination with suitable pharmaceutical auxiliaries, e.g. in the form of tablets, coated tablets, capsules, suppositories, patches, emulsions, suspensions, gels or solutions, the active compound content advantageously being between 0.1 and 95%.

The person skilled in the art is familiar on the basis of his/her expert knowledge with the auxiliaries which are suitable for the desired pharmaceutical formulations. In addition to solvents, gel-forming agents, ointment bases and other active compound carriers, it is possible, for example, to use antioxidants, dispersants, emulsifiers, preservatives, solubilizers or permeation promoters.

For the treatment of disorders of the respiratory tract, the compounds according to the invention are preferably also administered by inhalation. For this purpose, these are administered either directly as a powder (preferably in micronized form) or by atomization of solutions or suspensions which contain them. With respect to the preparations and administration forms, reference is made, for example, to the embodiments in European Patent 163 965.

For the treatment of dermatoses, the compounds according to the invention are in particular administered in the form of those medicaments which are suitable for topical application. For the production of the medicaments, the compounds according to the invention (=active compounds) are preferably mixed with suitable pharmaceutical auxiliaries and processed to give suitable pharmaceutical formulations. Suitable pharmaceutical formulations which may be mentioned are, for example, powders, emulsions, suspensions, sprays, oils, ointments, fatty ointments, creams, pastes, gels or solutions.

The pharmaceuticals according to the invention are prepared by processes known per se. The active compounds are administered in the order of magnitude customary for PDE inhibitors. Thus topical application forms (such as, for example, ointments) for the treatment of dermatoses contain the active compounds in a concentration of, for example, 0.1–99%. The dose for administration by inhalation is customarily between 0.01 and 1 mg per burst of spray. The customary dose in the case of systemic therapy p.o. or i.v. is between 0.1 and 200 mg per administration.

Biological Investigations

In the investigation of PDE IV inhibition at the cellular level, the activation of inflammatory cells has particular importance. An example which may be mentioned is the FMLP (N-formyl-methionyl-leucyl-phenylalanine)-induced superoxide production of neutrophilic granulocytes, which can be measured as luminol-potentiated chemoluminescence [McPhail LC, Strum SL, Leone PA and Sozzani S, The neutrophil respiratory burst mechanism. In "Immunology Series" 57: 47–76, 1992; ed. Coffey RG (Marcel Decker, Inc., New York-Basle-Hong Kong)].

Substances which inhibit chemoluminescence and cytokine secretion and the secretion of proinflammatory mediators in inflammatory cells, in particular neutrophilic and eosinophilic granulocytes, are those which inhibit PDE IV. This isoenzyme of the phosphodiesterase families is particularly represented in granulocytes. Its inhibition leads to the raising of the intracellular cyclic AMP concentration and thus to the inhibition of cellular activation. PDE IV inhibition by the substances according to the invention is thus a central indicator of the suppression of inflammatory processes. (Giembycz MA, Could isoenzyme-selective phosphodiesterase inhibitors render bronchodilatory therapy redundant in the treatment of bronchial asthma? Biochem Pharmacol 43: 2041–2051, 1992; Torphy TJ et al., Phosphodiesterase inhibitors: new opportunities for treatment of asthma. Thorax 46: 512–523, 1991: Schudt C et al., Zardaverine: a cyclic AMP PDE III/IV inhibitor. In "New Drugs for Asthma Therapy", 379–402, Birkhauser Verlag Basle 1991; Schudt C et al., Influence of selective phosphodiesterase inhibitors on human neutrophil functions and levels of camp and Cai. Naunyn-Schmiedebergs Arch Pharmacol 344: 682–690, 1991; Nielson CP et al., Effects of selective phosphodiesterase inhibitors on polymorphonuclear leukocyte respiratory burst. J. Allergy Clin Immunol 86: 801–808, 1990; Schade et al., The specific type III and IV phosphodiesterase inhibitor zardaverine suppresses formation of tumor necrosis factor by macrophages. European Journal of Pharmacology 230: 9–14, 1993).

1. Inhibition of the PDE IV activity

Method

The activity test was carried out according to the method of Bauer and Schwabe, which was adapted to microtiter plates (Naunyn-Schmiedeberg's Arch. Pharmacol. 311, 193–198, 1980). In this test, the PDE reaction is carried out in the first step. In a second step, the resulting 5'-nucleotide is cleaved by a 5'-nucleotidase of the snake venom from Ophiophagus hannah (king cobra) to give the uncharged nucleoside. In the third step, the nucleoside is separated from the remaining charged substrate on ion-exchange columns. The columns are eluted with 2 ml of 30 mM ammonium formate (pH 6.0) directly into minivials into which 2 ml of scintillator fluid is additionally added for counting.

The inhibitory values determined for the compounds according to the invention follow from Table 1 below, in which the numbers of the compounds correspond to the numbers of the examples.

TABLE 1

| Inhibition of the PDE IV activity | |
|---|---|
| Compound | −log $IC_{50}$ |
| 1 | 7.75 |
| 2 | 7.09 |

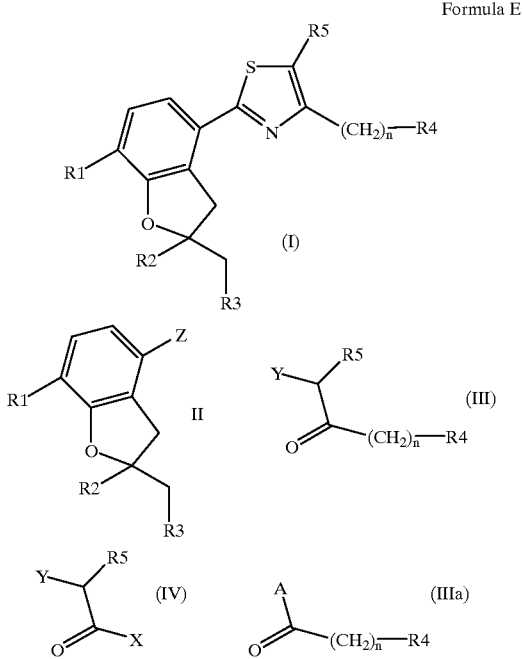

Formula E

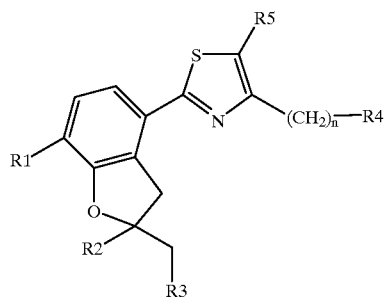

We claim:
1. Compounds of the formula I

(I)

in which
R1 is 1-4C-alkoxy, 3-7C-cycloalkoxy, 3-7C-cycloalkylmethoxy, benzyloxy or 1-4C-alkoxy which is completely or mainly substituted by fluorine,
R2 is hydrogen or 1-4C-alkyl and
R3 is hydrogen or 1-4C-alkyl, or
R2 and R3, together and including the two carbon atoms to which they are bonded, are a 5-, 6- or 7-membered hydrocarbon ring, optionally interrupted by an oxygen atom,
R4 is a phenyl ring substituted by R41, R42 and R43, a mono- or bicyclic heterocycle substituted by R44, R45 and R46, which is selected from the group consisting of pyridine, pyrrole, quinoline, isoquinoline, indole, isoindole, indolizine, pyrimidine, pyrazine, pyridazine, quinoxaline, quinazoline, cinnoline, benzimidazole, thiophene and furan or a heterocycle substituted by R44 and R45, which is selected from the group consisting of pyrazole, imidazole, oxazole, isoxazole, thiazole and isothiazole, where
R41 is hydrogen, carboxyl, 1-4C-alkoxycarbonyl, carbamoyl, hydroxysulfonyl, sulfamoyl, mono- or di-1-4C-alkylaminocarbonyl, mono- or di-1-4C-alkylaminosulfonyl, amino, mono- or di-1-4C-alkylamino, 1-4C-alkylcarbonylamino, 1-4C-alkylsulfonyl, 1-4C-alkoxysulfonyl, hydroxy-1-4C-alkyl, hydroxyl, 1-4C-alkoxy, 1-4C-alkyl, 1-4C-alkylcarbonyl, 1-4C-alkylcarbonyloxy, halogen, cyano or nitro,
R42 is hydrogen, hydroxyl, amino, mono- or di-1-4C-alkylamino, 1-4C-alkylcarbonylamino, nitro, halogen, 1-4C-alkoxycarbonyl, 1-4C-alkylcarbonyloxy, 1-4C-alkylcarbonyl, carboxyl, 1-4C-alkyl or 1-4C-alkoxy,
R43 is hydrogen, 1-4C-alkoxy, halogen or hydroxyl,
R44 is hydrogen, carboxyl, 1-4C-alkoxycarbonyl, carbamoyl, hydroxysulfonyl, sulfamoyl, mono- or di-1-4C-alkylaminocarbonyl, mono- or di-1-4C-alkylaminosulfonyl, amino, mono- or di-1-4C-alkylamino, 1-4C-alkylcarbonylamino, hydroxy-1-4C-alkyl, hydroxyl, 1-4C-alkoxy, 1-4C-alkyl, 1-4C-alkylcarbonyl, 1-4C-alkylcarbonyloxy, halogen, cyano or nitro,
R45 is hydrogen, hydroxyl, halogen, carboxyl, amino, 1-4C-alkyl, 1-4C-alkylcarbonyl, 1-4C-alkoxycarbonyl or 1-4C-alkoxy and
R46 is hydrogen, halogen, 1-4C-alkoxy or 1-4C-alkyl,
R5 is hydrogen or halogen,
n is 0, 1 or 2,
a salt thereof an N-oxide of a pyridine, quinoline, isoquinoline, pyrimidine, pyrazine, imidazole, quinoxaline, quinazoline or benzimidazole salt thereof.
2. Compounds of the formula I as claimed in claim 1, in which
R1 is 1-4C-alkoxy, 3-5C-cycloalkoxy, 3-5C-cycloalkylmethoxy or 1-4C-alkoxy which is completely or mainly substituted by fluorine,
R2 is 1-4C-alkyl and
R3 is hydrogen or 1-4C-alkyl, or
R2 and R3, together and including the two carbon atoms to which they are bonded, are a cyclopentane, cyclohexane, tetrahydrofuran or tetrahydropyran ring,
R4 is a phenyl ring substituted by R41 and R42 or a mono- or bicyclic heterocycle substituted by R44 and R45, which is selected from the group consisting of pyridine, pyrrole, quinoline, isoquinoline, indole, isoindole, indolizine, pyrimidine, pyrazine, pyridazine, pyrazole, imidazole, quinoxaline, quinazoline, cinnoline, benzimidazole, oxazole, isoxazole, thiazole and isothiazole, where
R41 is hydrogen, carboxyl, 1-4C-alkoxycarbonyl, carbamoyl, hydroxysulfonyl, sulfamoyl, mono- or di-1-4C-alkylaminocarbonyl, mono- or di-1-4C-alkylaminosulfonyl, amino, mono- or di-1-4C-alkylamino, 1-4C-alkylcarbonylamino, 1-4C-alkylsulfonyl, 1-4C-alkoxysulfonyl, hydroxy-1-4C-alkyl, hydroxyl, 1-4C-alkoxy, 1-4C-alkyl, 1-4C-alkylcarbonyl, 1-4C-alkylcarbonyloxy, halogen, cyano or nitro,
R42 is hydrogen, hydroxyl, nitro, halogen, 1-4C-alkoxycarbonyl, 1-4C-alkylcarbonyloxy, 1-4C-alkylcarbonyl, carboxyl or 1-4C-alkoxy, R44 is hydrogen, carboxyl, 1-4C-alkoxycarbonyl, carbamoyl, hydroxysulfonyl, sulfamoyl, mono- or di-1-4C-alkylaminocarbonyl, mono- or di-1-4C-alkylaminosulfonyl, amino, mono- or di-1-4C-alkylamino, 1-4C-alkylcarbonylamino, hydroxy-1-4C-alkyl, hydroxyl, 1-4C-alkoxy, 1-4C-alkyl, 1-4C-alkylcarbonyl, halogen or cyano and R45 is hydrogen, hydroxyl, halogen, carboxyl, amino, 1-4C-alkyl or 1-4C-alkoxy, R5 is hydrogen or halogen, n is 0 or 1, the salt thereof an N-oxide of a pyridine, quinoline, isoquinoline, pyrimidine, pyrazine, imidazole, quinoxaline, quinazoline or benzimidazole or a salt thereof.

3. Compounds of the formula I as claimed in claim 1, in which

R1 is 1-4C-alkoxy, 3-5C-cycloalkoxy or 1-2C-alkoxy which is completely or mainly substituted by fluorine, R2 and R3, together and including the two carbon atoms to which they are bonded, are a cyclopentane or cyclohexane ring, R4 is a phenyl ring substituted by R41 and R42 or a mono- or bicyclic heterocycle substituted by R44 and R45, which is selected from the group consisting of pyridine, pyrrole, quinoline, isoquinoline, indole, isoindole and indolizine, where R41 is hydrogen, carboxyl, 1-4C-alkoxycarbonyl, carbamoyl, hydroxysulfonyl, sulfamoyl, mono- or di-1-4C-alkylaminocarbonyl, mono- or di-1-4C-alkylaminosulfonyl, amino, mono- or di-1-4C-alkylamino, 1-4C-alkylcarbonylamino, 1-4C-alkylsulfonyl, 1-4C-alkoxysulfonyl, hydroxy-1-4C-alkyl, hydroxyl, 1-4C-alkoxy, 1-4C-alkyl, 1-4C-alkylcarbonyl, 1-4C-alkylcarbonyloxy, halogen, cyano or nitro, R42 is hydrogen, hydroxyl, nitro, halogen, 1-4C-alkoxycarbonyl, 1-4C-alkylcarbonyloxy, 1-4C-alkylcarbonyl, carboxyl or 1-4C-alkoxy, R44 is hydrogen, carboxyl, 1-4C-alkoxycarbonyl, carbamoyl, hydroxysulfonyl, sulfamoyl, mono- or di-1-4C-alkylaminocarbonyl, mono- or di-1-4C-alkylaminosulfonyl, amino, mono- or di-1-4C-alkylamino, 1-4C-alkylcarbonylamino, hydroxy-1-4C-alkyl, hydroxyl, 1-4C-alkoxy, 1-4C-alkyl, 1-4C-alkylcarbonyl, halogen or cyano and R45 is hydrogen, hydroxyl, halogen, carboxyl, amino, 1-4C-alkyl or 1-4C-alkoxy, R5 is hydrogen, n is 0, a salt thereof, an N-oxide of a pyridine or a salt thereof.

4. Compounds of the formula I as claimed in claim 1, in which

R1 is 1-4C-alkoxy or 1-2C-alkoxy which is completely or mainly substituted by fluorine, R2 and R3, together and including the two carbon atoms to which they are bonded, are a cyclopentane ring, R4 is a phenyl ring substituted by R41 and R42 or pyridine substituted by R44 and R45, where R41 is hydrogen, carboxyl, 1-4C-alkoxycarbonyl, carbamoyl, hydroxysulfonyl, sulfamoyl, mono- or di-1-4C-alkylaminocarbonyl, mono- or di-1-4C-alkylaminosulfonyl, amino, mono- or di-1-4C-alkylamino, 1-4C-alkylcarbonylamino, 1-4C-alkylsulfonyl, 1-4C-alkoxysulfonyl, hydroxy-1-4C-alkyl, hydroxyl, 1-4C-alkoxy, 1-4C-alkyl, 1-4C-alkylcarbonyl, 1-4C-alkylcarbonyloxy, halogen, cyano or nitro, R42 is hydrogen, hydroxyl, nitro, halogen, 1-4C-alkoxycarbonyl, 1-4C-alkylcarbonyloxy, 1-4C-alkylcarbonyl, carboxyl or 1-4C-alkoxy, R44 is hydrogen, carboxyl, 1-4C-alkoxycarbonyl, carbamoyl, hydroxysulfonyl, sulfamoyl, mono- or di-1-4C-alkylaminocarbonyl, mono- or di-1-4C-alkylaminosulfonyl, amino, mono- or di-1-4C-alkylamino, 1-4C-alkylcarbonylamino, hydroxy-1-4C-alkyl, hydroxyl, 1-4C-alkoxy, 1-4C-alkyl, 1-4C-alkylcarbonyl, halogen or cyano and R45 is hydrogen, hydroxyl, halogen, carboxyl, amino, 1-4C-alkyl or 1-4C-alkoxy, R5 is hydrogen, n is 0, a salt thereof an N-oxide of a pyridine or a salt thereof.

5. Compounds of the formula I as claimed in claim 1, in which

R1 is 1-4C-alkoxy,

R2 and R3, together and including the two carbon atoms to which they are bonded, are a cyclopentane ring, R4 is a phenyl ring substituted by R41 or pyridine substituted by R44, where R41 is hydrogen, carboxyl, 1-4C-alkoxycarbonyl, carbamoyl, hydroxysulfonyl, sulfamoyl or hydroxyl and R44 is hydrogen, carboxyl, 1-4C-alkoxycarbonyl, carbamoyl, hydroxysulfonyl, sulfamoyl or hydroxyl, R5 is hydrogen, n is 0, or a salt thereof.

6. Compounds of the formula I as claimed in claim 1, in which

R1 is methoxy,

R2 and R3, together and including the two carbon atoms to which they are bonded, are a cyclopentane ring, R4 is a phenyl ring substituted by R41 or pyridine substituted by R44, where R41 is carboxyl or carbamoyl and R44 is hydrogen, carboxyl or 1-4C-alkoxycarbonyl, R5 is hydrogen, n is 0, or a salt thereof.

7. A medicament composition comprising an effective amount of a compound as claimed in claim 1, together with a customary pharmaceutical auxiliary and/or excipient.

8. A method of treating a subject prone to or afflicted with an airway disorder which comprises administering to such subject an effective amount of a compound of claim 1.

9. A method of treating a subject afflicted with an amenable dermatosis which comprises administering to such subject an effective amount of a compound of claim 1.

10. In a method for treating a condition which is amenable to treatment by a PDE inhibitor, the improvement which comprises administering an effective amount of a compound of claim 1 to a subject afflicted with such condition.

11. In a method for compounding a medicament composition comprising an effective amount of active ingredient for treating an airway disorder and a customary auxiliary and/or excipient, the improvement wherein the active ingredient is a compound of claim 1.

* * * * *